(12) United States Patent
Trompier (10) Patent No.: US 10,031,093 B2
(45) Date of Patent: Jul. 24, 2018

(54) RADICAL SPECIES, AND METHOD FOR MEASURING RECEIVED DOSES

(71) Applicant: Institut de Radioprotection et de Sûreté Nucléaire, Fontenay-aux-Roses (FR)

(72) Inventor: François Trompier, Fontenay aux Roses (FR)

(73) Assignee: Institut de Radioprotection et de Sûreté Nucléaire (FR)

( * ) Notice: Subject to any disclaimer, the term of this patent is extended or adjusted under 35 U.S.C. 154(b) by 12 days.

(21) Appl. No.: 15/105,956

(22) PCT Filed: Dec. 18, 2014

(86) PCT No.: PCT/EP2014/078421
§ 371 (c)(1),
(2) Date: Aug. 30, 2016

(87) PCT Pub. No.: WO2015/091767
PCT Pub. Date: Jun. 25, 2015

(65) Prior Publication Data
US 2016/0370308 A1   Dec. 22, 2016

(30) Foreign Application Priority Data
Dec. 18, 2013 (FR) .................. 13 62890

(51) Int. Cl.
*G01J 1/58* (2006.01)
*G01N 24/10* (2006.01)
(Continued)

(52) U.S. Cl.
CPC .......... *G01N 24/10* (2013.01); *A61N 5/1071* (2013.01); *G01N 33/4833* (2013.01); *G01N 33/6893* (2013.01)

(58) Field of Classification Search
CPC ........ A61K 38/015; A61B 2017/00716; A61N 5/1071; G01N 24/10; G01N 33/6893; G01N 33/4833; Y10S 514/844
(Continued)

(56) References Cited

U.S. PATENT DOCUMENTS

2004/0251899 A1   12/2004   Swartz et al.
2006/0194198 A1   8/2006   Licata
(Continued)

FOREIGN PATENT DOCUMENTS

WO   2010047879 A2   4/2010
WO   2010047879 A3   4/2010

OTHER PUBLICATIONS

Cestelli Guidi M et al: "In vivo skin leptin modulation after 14 MeV neutron irradiation: a molecular and FT-IR spectroscopic study", Analytical and Bioanalytical Chemistry, Springer, Berlin, DE, vol. 404, No. 5, Apr. 29, 2012 (Apr. 29, 2012), pp. 1317-1326.
(Continued)

*Primary Examiner* — Taeho Jo
(74) *Attorney, Agent, or Firm* — Lerner, David, Littenberg, Krumholz & Mentlik, LLP (57) ABSTRACT

The invention relates to a radiation-induced radical species characterized in that it has, when measuring a biological nail, hair, or stratum corneum tissue sample by continuous wave EPR spectroscopy at ambient temperature: a Lande factor of 2.004; during Q band measurements at ambient temperature, a minimum signal intensity and a maximum signal intensity, said intensities being reached for magnetic field values separated by 1.8 mT; during X band measurements, a signal forming a singlet; and at the highest frequency, a signal having Lande factor anisotropy. The invention also relates to methods suitable for the identified radical
(Continued)

species and intended for preparing a sample, analyzing the measured signal, and estimating a received dose.

11 Claims, 6 Drawing Sheets

(51) Int. Cl.
   *G01N 33/68* (2006.01)
   *A61N 5/10* (2006.01)
   *G01N 33/483* (2006.01)
(58) Field of Classification Search
   USPC ..................................................... 260/458.1
   See application file for complete search history.

(56) References Cited

U.S. PATENT DOCUMENTS

| | | | | |
|---|---|---|---|---|
| 2010/0331257 | A1* | 12/2010 | Bayon | A61K 38/1875 514/17.2 |
| 2011/0104052 | A1* | 5/2011 | Barnett | A61K 9/0019 424/1.21 |
| 2012/0040304 | A1* | 2/2012 | Swartz | G01R 33/60 433/29 |
| 2012/0112746 | A1* | 5/2012 | Hyde | G01N 24/10 324/316 |
| 2014/0050689 | A1* | 2/2014 | Pathak | A61K 35/12 424/78.3 |
| 2015/0018750 | A1* | 1/2015 | Ueda | A61Q 19/08 604/20 |
| 2016/0058689 | A1* | 3/2016 | Wada | A61Q 3/00 424/61 |

OTHER PUBLICATIONS

F. Trompier et al: "State of the art in nail dosimetry: free radicals identification and reaction mechanisms", Radiation and Environmental Biophysics, vol. 53. No. 2, Jan. 28, 2014 (Jan. 28, 2014), pp. 291-303.
French Search Report for French Application No. 1362890 dated Oct. 6, 2014.
Iliana Maria Ramirez et al: "Simulation of laser radiation effects on low dimensionality structures", Journal of Molecular Modeling, vol. 19. No. 5, Nov. 15, 2012 (Nov. 15, 2012), pp. 2091-2095.
International Search Report of Application No. PCT/EP2014/078421 dated Feb. 5, 2015.
Polyakov V et al: "Effect of mechanically induced background signal on EPR dosimetry of tooth enamel", Radiation Measurements, Elsevier, Amsterdam, NL, vol. 24. No. 3, Jul. 1, 1995 (Jul. 1, 1995), pp. 249-254.
Xiaoming He et al: "Advances towards using finger/toenail dosimetry to triage a large population after potential exposure to ionizing radiation", Radiation Measurements, Elsevier, Amsterdam, NL, vol. 46, No. 9, May 2, 2011 (May 2, 2011), pp. 882-887.

* cited by examiner

RADICAL SPECIES, AND METHOD FOR MEASURING RECEIVED DOSES

CROSS REFERENCE TO RELATED APPLICATIONS

The present application is a national phase entry under 35 U.S.C. § 371 of International Application No. PCT/EP2014/078421 filed Dec. 18, 2014, published in French, which claims priority from French Patent Application No. 1362890 filed Dec. 18, 2013, all of which are incorporated herein by reference.

FIELD OF THE INVENTION

The invention relates to the field of measuring the dose of ionizing radiations received by biological tissues.

The invention in particular relates to the preparation of biological tissues comprising keratin, in particular from tissues of the nails, hair, or skin-cornea type, for a dose measurement, and a method for determining a dose of a sample of such tissues including the preparation of the samples.

STATE OF THE ART

During radiological accidents, it is vital to estimate the received doses at the most exposed points. During a so-called entire body irradiation, where the totality of the body is exposed, the dose distribution in the organism is generally heterogenous. It is therefore important to determine the most exposed members or portions of the body and to determine the doses at the members the most sensitive to radiations. An external irradiation, at a strong dose, of a portion of the body, caused by ionizing radiations of the X, gamma, beta or neutron nature, is expressed inter alia by deterministic effects which appear from values of a certain value of doses. For example, at the skin, the effects may occur as an erythema to a necrosis of the tissues for doses greater than or equal to 25 Gy. In the case of partial irradiation of the body or localized irradiation (collimated field, handling of radioactive sources, . . . ), the doses may be locally very high and attain dose values of a few tens or hundred of Gy. The time-dependent change of the lesions is difficult to predict on the sole basis of the observations of clinical signs and an information on the dose and its distribution gives the possibility of targeting the irradiation level and of estimating the consequences on the body and of applying the most suitable treatments.

The determination of doses received by a sample of biological tissues may be applied with different methods, such as electronic paramagnetic resonance spectroscopy (EPRS) or luminescence which may be implemented with different stimulation methods from among thermal, chemical, optical methods, etc.

These techniques utilize the presence of free radicals or defects induced by the irradiation in a material, i.e. chemical species comprising at least one non-paired electron, defects, or ions which are generated after interaction of the material with ionizing radiations (photons, electrons, protons, neutrons, a particles, etc.).

For localized irradiations, for example on the hands in the case of an accident in the handling of radioactive sources, the dose distribution on the affected portion of the body may be very heterogenous, certain areas may locally receive doses attaining a few tens of Grays. In these cases, it is important to determine the maximum received doses and the most irradiated volumes of the body.

Under these situations, known dosimetric techniques prove to be poorly adapted. The techniques of biological dosimetry only allow an estimation of a dose of the entire body, which is not relevant. For example, the doses received by the hands can only be determined from measurements on bone biopsies. Techniques such as EPR spectroscopy can therefore only be used in the case of an amputation or if the samples may be taken during a surgical operation.

The taking of samples is therefore very invasive and does not give the possibility of easily obtaining several measurements of doses over different areas of a hand in order to establish a dose distribution.

Conducting dose measurements on the nails or hair has already been contemplated, but this measurement is complex in the nails because of the intrinsic signals from the nails, and of parasitic signals induced by the mechanical stress upon cutting the nails and in the hair because of the presence of melanin.

Further, the already identified radio-induced radical species in the nails and the hair are unstable and very sensitive to humidity, which prevents the application of this technique regardless of the circumstances.

In particular, the radical species identified earlier for conducting a dose measurement by detecting a radio-induced signal, being sensitive to humidity, the signal completely disappeared for example as soon as an individual had washed his/her hands. The same applies for the free radicals generated by the mechanical stress in the nails.

Figure 1A:
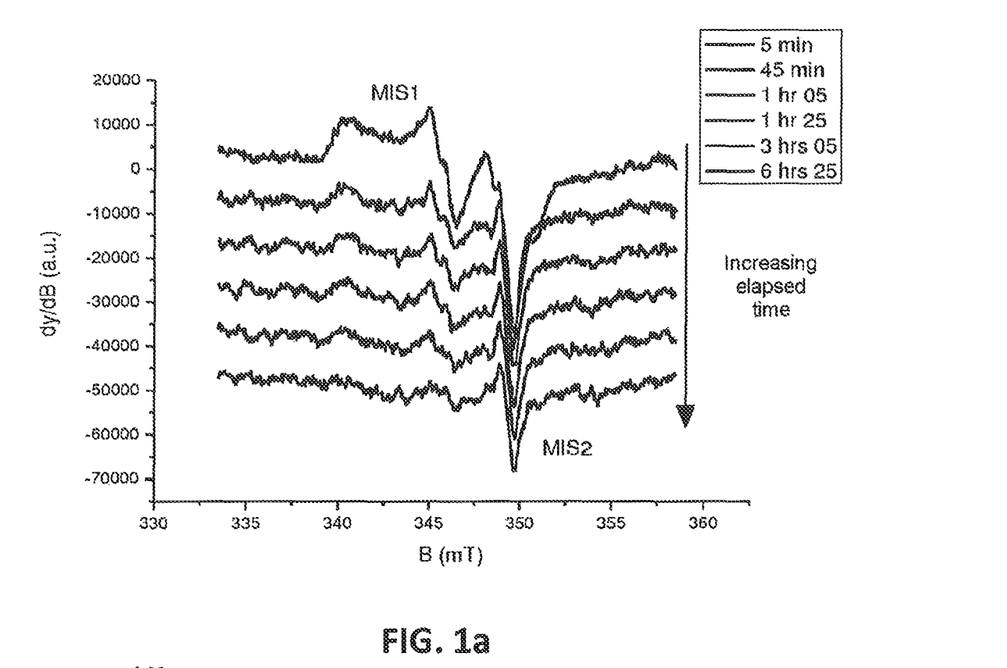
FIGS. 1a and 1b, already also described, illustrate the time-dependent change of the EPR spectroscopy response from nails having respectively been subject to mechanical stress and irradiation, as a function of a hydration duration.
Figure 1B:
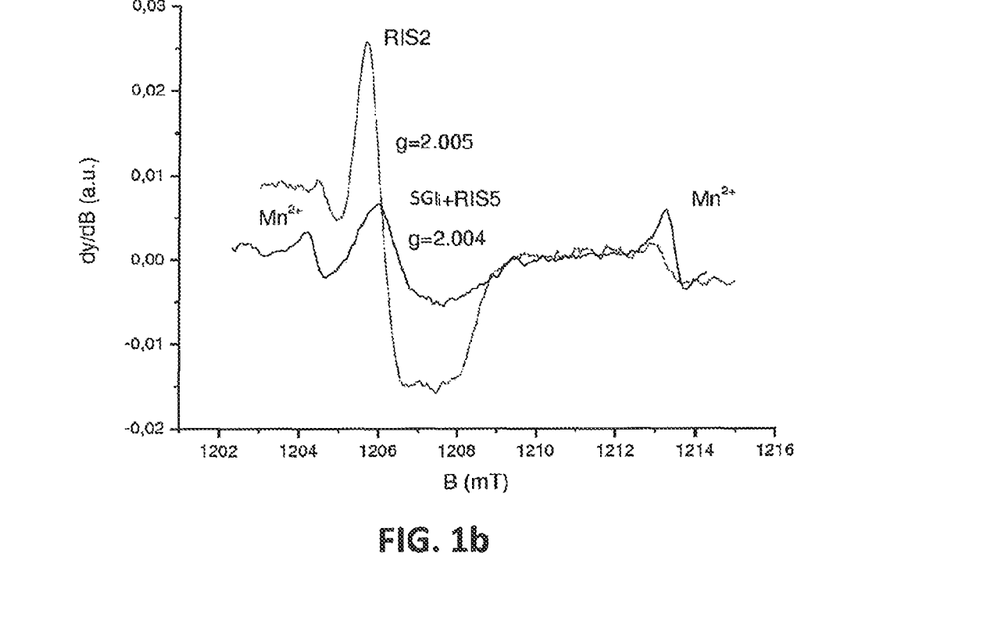

This characteristic is apparent in FIGS. 1a and 1b, which respectively show the response in EPR spectroscopy of nails having been subject respectively to a mechanical stress (cut, FIG. 1a) and to irradiation (FIG. 1b) as a function of a hydration duration.

Therefore there exists a need for proposing a reliable and non-invasive way for measuring a locally received dose, for example at the hands or at the feet with the toes/nails or at the head with the hair.

PRESENTATION OF THE INVENTION

An object of the invention is to propose a method for measuring a dose on biological tissues comprising keratin, notably tissues of the nails, hair, or cornea layer of the skin.

Another object of the invention is to propose a method for preparing biological tissues on which a dose measurement is applied, for improving the quality of the signal during the measurement.

In this respect, the object of the invention is a radio-induced radical species characterized in that it has, during the measurement of a biological tissue sample of the nail, hair or skin-cornea type by EPR spectroscopy in continuous waves at room temperature:

Landé factor of 2.004,
during measurements in a Q-band and at room temperature, a minimum signal intensity and a maximum signal intensity, said intensities being attained for magnetic field values separated by 1.8 mT,
during measurements in a X-band, a signal forming a singlet, and
at a higher frequency, a signal having a Landé factor anisotropy.

The radical species further has a signal intensity in EPR spectroscopy or in a dose measurement by increasing luminescence with a dose received by the tissue sample until it attains a saturation level, and then an expression level decreasing with the dose from said saturation level, down to an annihilation level.

The radical species further has a stable signal intensity with humidity and stable to within plus or minus 20% during exposure to a temperature of less than 180° C.

The object of the invention is also a method for preparing a sample of biological tissues having received a dose of ionizing radiations, comprising keratin, in particular tissues of the nail, hair or skin-cornea type, for a measurement of the dose, characterized in that it comprises:

hydration of the sample for a period of more than 5 minutes, and controlled dehydration of the sample.

Advantageously, but optionally, the method for preparing a sample further comprises at least of the following features:

the controlled dehydration of the hydrated sample comprises the drying of said sample in a drier for a period of more than 10 hours, preferably equal to 15 hours for EPR spectroscopy measurements in the Q-band.

the hydrated sample of biological tissues is installed in the drier in vacuo with an amount of desiccant material, said material preferably being silica gel.

the mass of the sample before hydration is comprised between 2 and 5 mg, and the hydration period is preferably equal to 10 minutes.

Another object of the invention consists in a method for determining a dose received by a sample prepared by the method according to the preceding description, the method comprising:

a) applying measurement of a radio-induced signal, followed by irradiation of the sample, in a repeated way until an intensity reference level of the signal is attained, b) determining an absolute value of received dose by at least one reference sample, corresponding to the intensity reference level of the signal, and c) determining the dose level initially received by the first sample as being the subtraction, from the value of the dose received by the reference sample, of the total dose added to the initial dose of the first sample during the application of step a).

Advantageously, but optionally, the method for determining a dose according to the invention may further comprise at least one of the following features:

the reference level is a saturation level of the intensity of the signal with the received dose or annihilation level of the signal.

the method further comprises a preliminary step comprising:

applying a measurement of radio-induced signal on the sample for which the intention is to determine the dose received for obtaining a first signal intensity, irradiation of the sample at a dose of less than 5 Gy, preferably less than 1 Gy, applying a second measurement on the sample in order to obtain a second signal intensity, and comparison of the intensities of both intensities for inferring therefrom an estimation of initial dose level received by the sample relatively to a dose level corresponding to a saturation level of the signal intensity.

the sample is prepared by the preparation method according to the earlier description after each irradiation of step a).

the technique for measuring the radio-induced signal intensity applied is EPR spectroscopy or measurement by luminescence.

the step b) of determining a dose value received by a reference sample corresponding to the reference level of signal intensity is applied from a curve relating absolute values of doses received by the reference sample with signal intensity levels, said curve being produced:

by averaging curves generated from measurements on biological tissues from a plurality of individuals, from measurements conducted on non-irradiated biological tissues from the same individual as the first sample, or from measurements conducted on irradiated biological tissues from the same individual as the first sample, said measurements being applied by measuring thermoluminescence after step a), and the first sample having been heated between step a) and said measurements for suppressing the initial radio-induced signal.

each curve is generated by one of the following processes:

cutting out a reference sample into a plurality of fragments and applying, on the fragments, irradiations at distinct and determined doses, and measuring a radio-induced signal intensity in the sample for each dose, applying successive irradiations of the reference sample at known doses, each irradiation being followed by a measurement of radio-induced signal intensity, or applying successive irradiations at distinct and determined doses, each irradiation being followed by a measurement of radio-induced signal intensity by measuring thermoluminescence, and then by heating of the sample for suppressing the radio-induced signal.

According to another embodiment, the invention also relates to a method for determining a dose received by a sample by applying a process with dosed additions or by comparison of a radio-induced signal of the sample measured by EPR spectroscopy or by luminescence measurement with a pre-established calibration curve, characterized in that it comprises, for each radio-induced signal measurement conducted on a sample, the determination of the contributions of the intrinsic signal of the sample and of the signal of a radio-induced radical species according to the invention.

Advantageously, but optionally, this method for determining a dose may further comprise at least one of the following features:

the tissue sample is a sample of nails, and the determination of the contributions of the intrinsic signal of the sample and of the radio-induced radical species comprises the measurement of a radio-induced signal of the sample for a same dose received by the sample, after two distinct hydration periods, and the inference, from the measurements, of the contributions of the intrinsic signal and of the radio-induced species signal.

the tissue sample is a sample of nails, and the determination of the contributions of the intrinsic signal of the sample and of the radio-induced radical species comprises the measurement of a radio-induced signal of the sample before and after exposure to a beam of ultrasonic waves for a determined duration, and inference of said contributions from the measurements.

the determination of the contributions of the intrinsic signal of the sample and of the radio-induced radical species comprises the measurement of a radio-induced signal of the sample after exposure to micro-waves at a first power, and exposure to micro-waves at a second power, greater than the first, and the inference of said contributions from the measurements.

According to another embodiment, the invention relates to a process for determining risks of developing skin lesions in a subject having received external irradiation, said process including steps consisting of:
i. estimating or determining the received dose by applying the preceding method, and
ii. determining depending on the dose of step i) the probability of occurrence of external lesions.

Another embodiment of the invention relates to a method for choosing a therapy to be provided to a subject having received external irradiation, said method comprising steps:
i. determining the risks of developing skin lesions in said subject, and
ii. selecting a therapy considering the risks determined in step i).

The identified radical species has high stability to humidity and to temperature, unlike the other radical species identified earlier.

The method for preparing the sample of biological tissues therefore gives the possibility of improving the quality of the signal measured after irradiation. Indeed, the unstable radical species resulting from a mechanical stress or from irradiation have an expression level greater than that of the radio-induced radical species which has been identified, thereby concealing, during a measurement, the radio-induced signal by this species.

The humidification of the sample therefore gives the possibility of removing all the unstable species so as to exclusively find the signals of the stable species.

Next, controlled dehydration of the tissues gives the possibility of making the measurements reproducible and comparable from one sample to the other, since the tissues have a thermally stable intrinsic signal but for which the intensity increases with the drying period of the tissues.

Methods for determining a dose have also been adapted to the particular characteristic of the variation of the intensity of the intrinsic signal SGI depending on the hydration level of the nail and because of the variability between the samples of the intensity of the intrinsic signal SGI.

Conventional dose measurement methods (calibration curves or dosed additions) require the determination of the component of the intrinsic signal SGI of the nails or of the intrinsic signal of melanin or of all the other intrinsic signals in the measured signal or its selective removal for estimating the intensity of the RIS5 in the measured signal.

DESCRIPTION OF THE FIGURES

Other features, objects and advantages of the invention will become apparent from the following description, which is purely illustrative and non-limiting, and which should be read with reference to the appended drawings wherein.

DETAILED DESCRIPTION OF AT LEAST ONE EMBODIMENT OF THE INVENTION

The invention is based on the identification of a radical species having substantial stability to humidity and to temperature, this species being induced during the irradiation of a biological tissue sample comprising keratin of the nail, hair or corneal layer of the skin (stratum corneum) type.

This radical species is characterized by its spectroscopic characteristics, which are the following:
its Landé factor g is equal to 2.004,
during a signal measurement by continuous wave EPR spectroscopy in the Q-band (34 GHz) at room temperature, this species produces a signal having a minimum and a maximum, the difference in magnetic field between these extrema being of 1.8 mT.

Other features are described in more details hereafter, which are:
the stability of the signal of the RIS5 species to humidity,
the stability of the signal of the species RIS5 to temperature, and
the particular characteristic of the signal of the RIS5 species depending on the received dose.

This species will subsequently be called RIS5.

This species had not been detected up till now since the intensity of its signal (EPR or luminescent signal), subsequent to the irradiation of a tissue sample, is of a low intensity notably as compared with the expression level of species which are radio-induced or induced by a mechanical stress with a same measurement technique, such as for example EPR spectroscopy or luminescence.

Further, the signal of this species RIS5 has similar characteristics to the intrinsic signal of the tissue which pre-exists at any irradiation or any mechanical stress, and which is called SGI subsequently.

The stability to humidity gives the possibility of proposing a method 100 for preparing such biological tissues, which improves the quality of the measured signal during a dose measurement.

Figure 2:
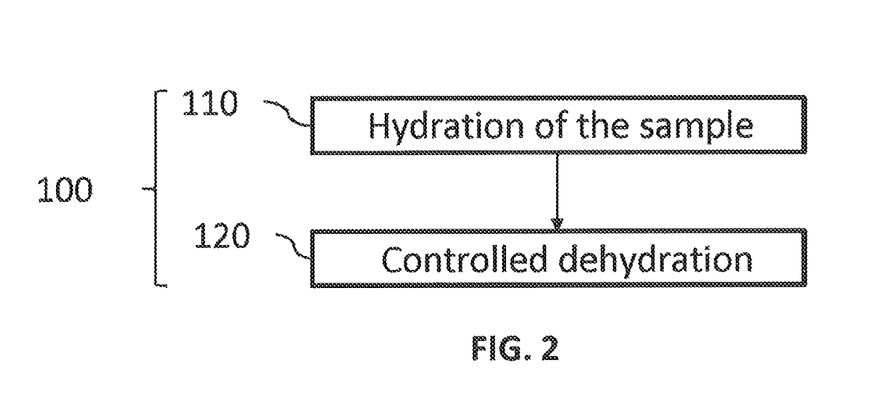
FIG. 2 illustrates the main steps of a method for preparing a sample of biological tissues for dose measurement.

The main steps of this method are illustrated in FIG. 2.

A first step consists of hydrating 110 the sample of biological tissues. This step allows suppression of the radio-induced unstable species or species induced by the mechanical stress, so as to only measure the signal from the RIS5 species and the intrinsic SGI signal. This also minimizes the SGI intrinsic signal of the tissue.

This hydration, or humidification, comprises the contacting of the samples of tissues with an aqueous medium, preferably for a duration greater than at least 5 minutes. Preferably, the tissues are immersed for this period in distilled water.

The hydration period is adapted depending on the relevant sample: depending on the thickness of the sampled tissues, on the sample date, etc.

The biological tissues suitable for applying the method of the invention are tissues containing keratin. By "keratin", is meant here a cytoplasm protein which is found in the cells of the epithelia, tissues forming the surface layer of the skin (epidermis) and mucosas. Keratin is particularly abundant in the surface layer of the epidermis, which is called the corneal layer, and in its annexes, the appendages (bristles, eyelashes, hairs, nails). The biological tissues of the method according to the invention are therefore preferably selected from nails, hairs and the skin corneal layer (stratum corneum).

For a sample for which the mass is comprised between 2 and 5 mg, the hydration period is preferably comprised between 5 and 20 minutes, and advantageously equal to 10 minutes, so as to result in a compromise between the suppression of the unstable free radicals and the application duration of the preparation method.

Figure 3A:
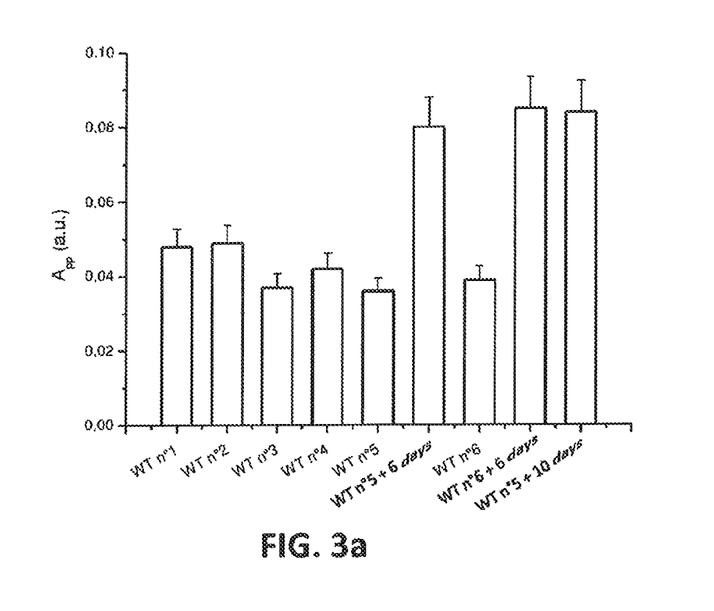
FIGS. 3a and 3b illustrate the time-dependent changes in the EPR signals for the radical species, and in the intrinsic signal and RIS5 (stable radio-induced signal) depending on the hydration or on the drying of the sample.

The method then comprises a step 120 for controllably drying the samples, so as to attain a determined hydration level. Indeed, as visible in FIG. 3a, the intensity of the intrinsic signal SGI for the nails increases with the dehydration period of the tissues, the data of FIG. 3a being provided after a humidification treatment "WT" followed by a drying period in air (for example WT no. 6+6 days means a sixth treatment with water followed by a period of 6 days for drying in air).

Figure 3B:
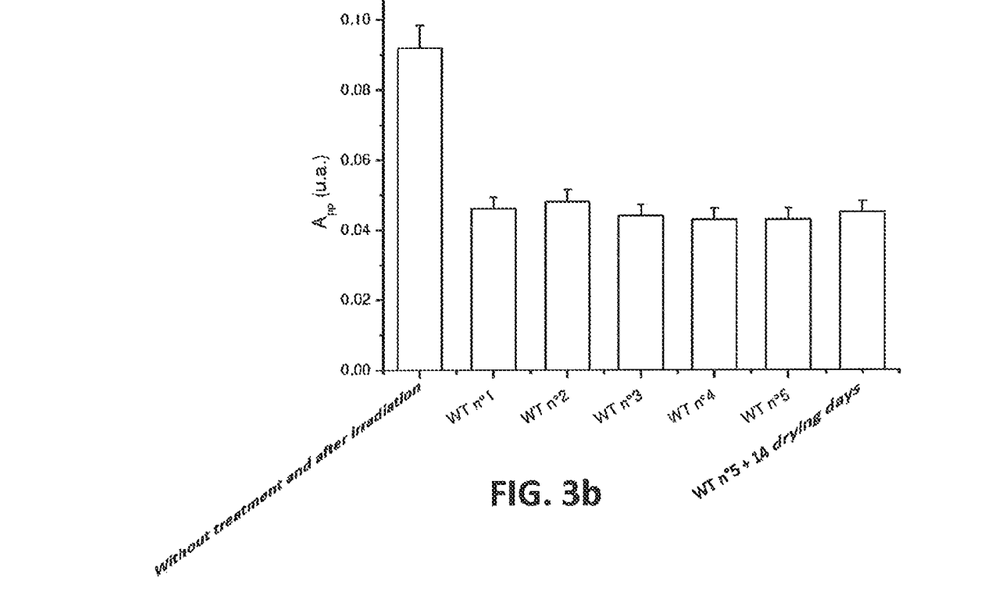

On the other hand, as illustrated in FIG. 3b, the humidification followed by drying has only a small influence on the intensity of the signal of the RIS5 species in the sample, which is shown in the figure by its EPR signal (peak-to-peak amplitude, measured at a dose level of the sample corresponding to a maximum expression of the RIS5 species relatively to the intrinsic signal SGI, i.e. of about 45 Gy): the first hydration generates a decrease in the intensity because of the presence of unstable radicals (removed by hydration) but the subsequent hydrations and dryings do not modify its intensity.

Figure 3C:
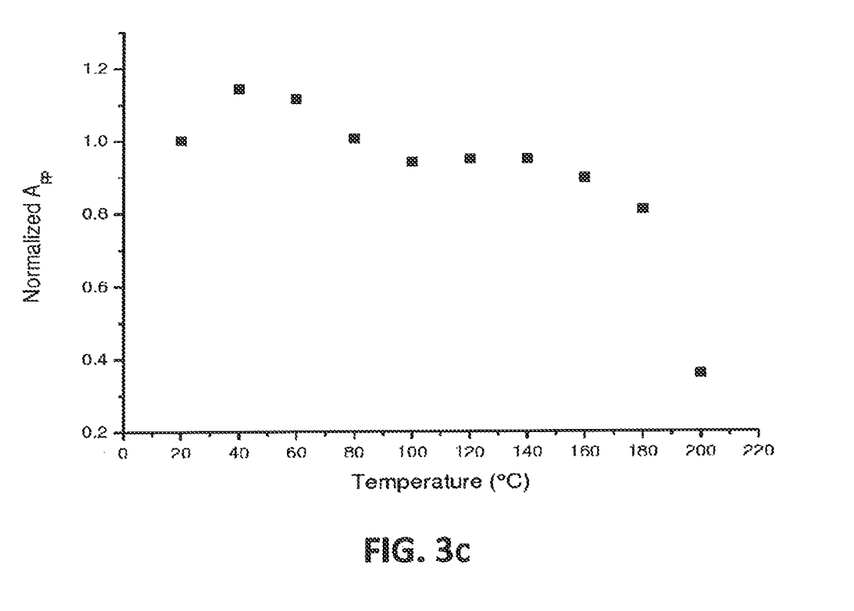
FIG. 3c is a curve illustrating the thermal stability of the signal of the species RIS5 by an isochronous thermal annihilation method.

This heat stability of the RIS5 species is also visible in FIG. 3c, which is an isochronous curve produced by measuring the signal of the RIS5 species after plateaus of 20 minutes during which the sample is exposed to temperatures increasing in a step of 20° C. It is seen that the signal is stable to within plus or minus 20% up to a temperature of 180° C.

It is therefore necessary, so that the method is reproducible and allows comparison of the signals measured on different samples, that in the case of nails, the contribution of the intrinsic signal SGI be identical from one measurement to the other, all the more so since this contribution may represent a substantial proportion, up to 90% of the signal for an irradiation of a few Grays.

Advantageously, the drying step is applied by placing the tissue sample in a drier (drying under vacuum). The required drying period depends on the type of conducted measurement. For example, an EPR spectroscopy measurement in a Q-band will require a longer drying period than a measurement in the X-band because of the greater sensitivity to humidity of the measurement in a Q-band. For example, in a Q-band for nails, a compromise between the sensitivity of the measurement and the minimization of the intensity of the SGI signal corresponds to a period of at least 10 hours, preferably of the order of 15 hours in the drier.

The sample is placed with a desiccant material like silica gel, or a gel of silica.

Alternatively, the sample may be heated to a controlled temperature, for a determined period of time.

Figure 4:
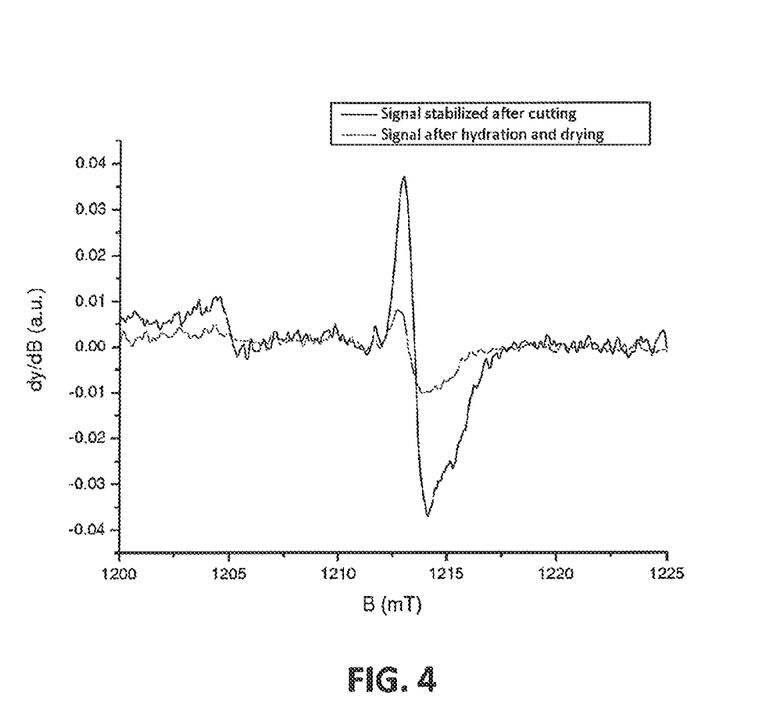
FIG. 4 illustrates the response in EPR spectroscopy of a cut nail and of a nail treated according to the preparation method.

The response by EPR spectroscopy of a thereby treated nail is illustrated in FIG. 4a, as compared with a cut but untreated nail. It is noticed that a substantial proportion of the signal has been suppressed.

Figure 5:
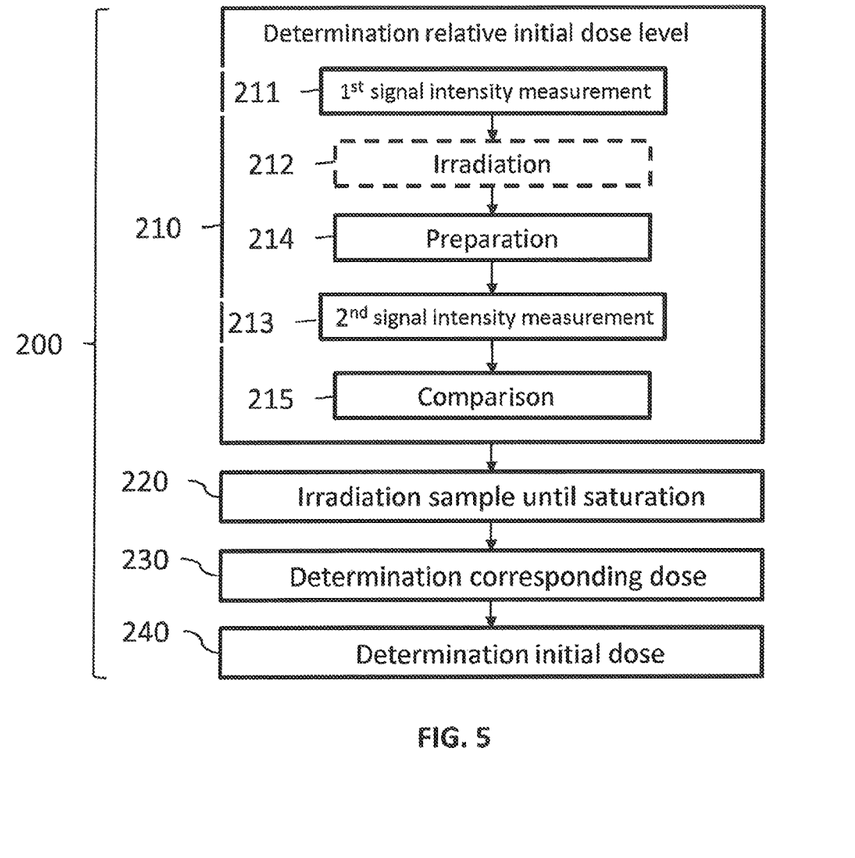
FIG. 5 illustrates the main steps of a method for determining a dose by EPR spectroscopy.

With reference to FIG. 5, a method for determining a dose received by a sample of biological tissues comprising keratin, which comprises after irradiation the RIS5 species will now be described.

The RIS5 radio-induced species used for dose detection has a particular feature: the intensity of the signal is not linear with the dose received by the sample of tissues, like the radical species currently utilized for dose measurement. The RIS5 measured signal on the contrary has an area increasing with the dose until attaining a so-called saturation level, beyond which an additional received dose causes a decrease in the intensity of the signal of the RIS5.

Figure 6:
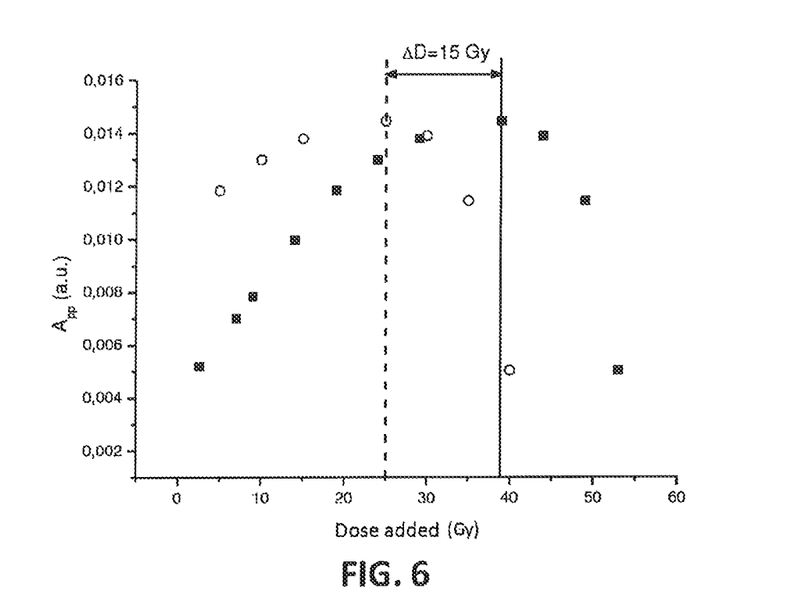
FIG. 6 illustrates the time-dependent change in the intensity of the EPR signal of the species R15 as a function of a received dose.

The intensity of the signal of the species RIS5 as a function of the dose received by the sample is illustrated in FIG. 6 with measurements conducted in EPR spectroscopy for both samples: the first sample, for which the values are illustrated with solid squares, was not irradiated at the origin, and underwent post-irradiations for tracking the time-dependent change of the signal versus the dose. The second sample, for which the values are illustrated by circles, underwent an initial dose of 15 Gy for simulating accidental exposure to radiations, before being irradiated again in order to track the time-dependent change of the signal versus the dose.

An original method 200 for determining the dose is proposed on the basis of the comparison of the characteristics of the variation curve of the intensity of the signal corresponding to RIS5 and to the intrinsic signal SGI in the case of nails (of the signal RIS5 and of the melanin signal for hair) of the analyzed sample with that of a virgin sample.

The features may for example be the saturation dose of RIS5 or the dose for annihilating the RIS5 (dose for which the measured signal intensity is canceled out and no longer varies with an additional dose). This method has the advantage of not having to determine the intensity of the intrinsic signal SGI for estimating the intensity of the RIS5 like with conventional methods for determining the dose.

The method 200, the steps of which are illustrated in FIG. 5, gives the possibility of estimating the dose received by the sample in an adapted way to this particular behavior, and notably from the behavior of intensity saturation from a certain dose.

This method comprises a first step 220, which comprises the application of successive irradiations of the sample with known doses, each irradiation being followed by a measurement of the intensity of the radio-induced signal, until the intensity of the radio-induced signal attains a determined level. This level, called a reference level, is highly advantageously the intensity saturation level or annihilation level since these levels are simple to identify—the saturation level because of the low variation of the intensity during its inflexion, and the annihilation level because of the cancelling out of the signal—and especially they are attained for a single dose value, unlike the other intensity levels, which are attained for two dose values (before and after irradiation respectively).

Alternatively, this level may be an intensity level below the saturation level, and attained for a dose smaller or greater than the dose corresponding to the saturation level.

Advantageously in this case, step 220 comprises a preliminary step for determining 210 a relative initial dose level received by the sample as compared with the dose level corresponding to the saturation of the expression level of RIS5.

This determination comprises the application 211 of a first intensity measurement of a radio-induced signal on the sample in order to obtain a first signal intensity.

Next, after the first irradiation of step 220, or an irradiation 212 being applied separately before step 220, this irradiation preferably being at a small dose, preferably less than 10 Grays, and preferably less than 5 Grays, for example equal to 1 Gray, a second intensity measurement 213 of a radio-induced signal on the sample is applied in order to obtain a second signal intensity. Preferably, between the irradiation 212 and the measurement 213, the irradiated sample is again prepared 214 by the method 100 described herein before in order to suppress the unstable components.

By comparing 215 both intensities of the measured signals, it is possible to determine whether the initially received dose by the sample is greater or less than the corresponding dose level at the intensity saturation of the expression of RI5.

Indeed, if the second signal has intensity greater than the first signal, this means that the initial dose received by the sample is less than the dose corresponding to the intensity saturation level. This corresponds to a dose level of the order of a few Grays, or at most of the order of a few tens of Grays, for example less than 40 or 50 Grays.

On the contrary, if the second signal has intensity below that of the first signal, this means that the initial dose of the sample is greater than the dose corresponding to a saturation level. This corresponds to a dose level of the order of a few tens of Grays, for example greater than 40 to 50 Grays.

The dose level corresponding to saturation imposes the selection of the dose used for irradiation of step 212, since the risk of exceeding the dose level corresponding to saturation has to be minimized.

This preliminary step is advantageously applied for making sure that the initial dose level received by the sample is less than the saturation level, in which case the reference intensity level used for estimating the dose is then preferably the saturation level. If it is determined that the initial dose level is greater than the saturation level, the reference intensity level used may be the annihilation level.

Returning to FIG. 5, once the additional dose has been determined in step 220 in order to have the sample exhibit the reference level of the signal, the method then comprises a step 230 consisting of determining the absolute value of the received dose by another sample, a so-called reference sample, so that the radio-induced signal measured for this dose corresponds to the reference level of the signal.

The reference sample is assumed to be non-irradiated initially.

For this, several methods are possible.

A first embodiment consists of generating a calibration curve from samples of similar tissues from different persons, the samples not having been irradiated initially.

For each individual, a received dose/measured radio-induced signal intensity curve may be built by successive additions of determined doses, the signal being measured between each new irradiation—and the sample being prepared again for measuring a dose with the method 100 described hereinbefore, before each measurement. The measurement technique may in this case be EPR spectroscopy, luminescence measurement or any other known technique.

Alternatively, a curve may also be generated by splitting a sample into several fragments, and by irradiating each fragment at known different doses. The radio-induced signal intensity of each fragment is then measured with the same technique in order to obtain a curve relating the various doses to various intensities.

Still according to an embodiment, a curve may be produced by applying successive irradiations at distinct and determined doses, each irradiation being followed by a measurement of radio-induced signal intensity by measuring thermoluminescence, and then by additional heating of the sample for suppressing the radio-induced signal.

The calibration curve is then generated by averaging the curves obtained for the various individuals.

Alternatively, the Applicant noticed that the dose level corresponding to an intensity saturation of the expression level of RIS5 is constant for the various biological tissues of a same nature of a same individual, for example for the different nails of a same individual.

Instead of producing a calibration curve from samples from a population of individuals, it is therefore advantageous to produce a signal intensity/dose curve from a tissue sample of the same individual, preferably it being assumed that it was not irradiated.

For example if the tissue sample for which the dose is intended to be measured stems from a nail of the hand, since the latter underwent irradiation because of an accidental handling of a source, it may be advantageous to build a curve from a nail sample from a toe.

The curve itself may be built according to the techniques described herein before for the curves being used for producing the calibration curve. Advantageously, if the radio-induced signal measurements are thermoluminescence measurements, it is advantageous to heat the sample being used for generating the curve in order to suppress the possible radio-induced signals which may however pre-exist.

Thus, it is possible to determine the total dose level received by a sample in order to attain the reference level of the radio-induced signal.

Returning to FIG. 5, during a step 240, the initial dose level received by the first sample is determined by subtracting from the absolute value of the dose received by the reference sample (corresponding to the reference level in intensity attained during step 220), the total dose level added to the first sample during step 220.

Each step for measuring an intensity level of a radio-induced signal may be applied by one of the known techniques from among which EPR spectroscopy, the latter being preferably applied in the Q-band, i.e. when the sample is subject to an electromagnetic beam with a frequency comprised between 33 and 50 GHz, or the luminescence measurement, advantageously by heat activation (measurement of thermoluminescence). The EPR in the Q-band has the advantage of better sensitivity for samples of small volumes.

Alternatively to the method 200, it is possible to use conventional dosing methods such as for example:

the so-called standard addition method, which consists of producing a first intensity measurement of a signal, for example by EPR spectroscopy or by luminescence, and then of carrying out a series of post-irradiations of the sample at known doses and of repeating the signal intensity measurements. The variation of the signal intensity versus the variation of a dose received is then measured for establishing a sensitivity coefficient and for inferring therefrom the initially absorbed dose, the method by comparing a measured signal intensity for the received dose to be determined relatively to a pre-established calibration curve.

In order to apply these methods, it is however necessary to be able to estimate the respective contributions of RIS5 and of the intrinsic signals or selectively remove these intrinsic signals, both types of signals having the same EPR signal characteristics in the X- and Q-band or in luminescence. Several approaches may be considered:

1. In the specific case of nails, since the intensity of the RIS5 signal does not change over time after hydration, unlike the intrinsic signal SGI which increases until it attains a constant value, it is therefore possible, by conducting measurements at different times after hydration, to estimate the respective components of the RIS5 and of the intrinsic signal. Taking into account the difference in behavior of the intrinsic signal and of the RIS5 after humidification, it is theoretically possible to estimate the contribution of each signal in the measured signal at g=2.004 by measuring this signal after humidification (A1) and after stabilization of the intrinsic signal (A2) wherein the Applicant has identified that the amplitude of the intrinsic signal SGI is multiplied by an average factor of 2.2. Indeed, we then have a system of two equations with two unknowns (Equ. 1), which is easily solved (Equ. 2).

$$\begin{bmatrix} A_1 = (A_{intrinsic\ signal} + A_{RIS5}) \\ A_2 = (2.2 \times A_{intrinsic\ signal} + A_{RIS5}) \end{bmatrix} \quad \text{Equation 1}$$

and $$\begin{bmatrix} A_{intrinsic\ signal} = \frac{(A_2 - A_1)}{1.2} \\ A_{RIS5} = \frac{(A_2 - 2.2 \times A_1)}{2} \end{bmatrix} \quad \text{Equation 2}$$

with A1 the amplitude of the signal at g=2.004 measured 12 hours after humidification and A2 the one measured after stabilization.

This approach may be applied regardless of the measurement technique (EPR spectroscopy, luminescence, etc.).

2. In the specific case of nails, it is possible to use ultrasonic waves for differentiating the RIS5 and SGI signals. The use of ultrasonic waves has the effect of reducing the intensity of RIS5 and of the intrinsic signal SGI but in different proportions. For example, an exposure of 45 minutes to ultrasonic waves (35 kHz, with samples in distilled water at 25° C.) allows reduction in the intensity of the intrinsic signal by a factor 5 and of that of RIS5 by a factor 10. In the same way as earlier, by conducting a measurement before and after treatment, with the system of two equations of two unknowns, it is possible to estimate the respective components of the intrinsic signal and of RIS5.

Figure 7:
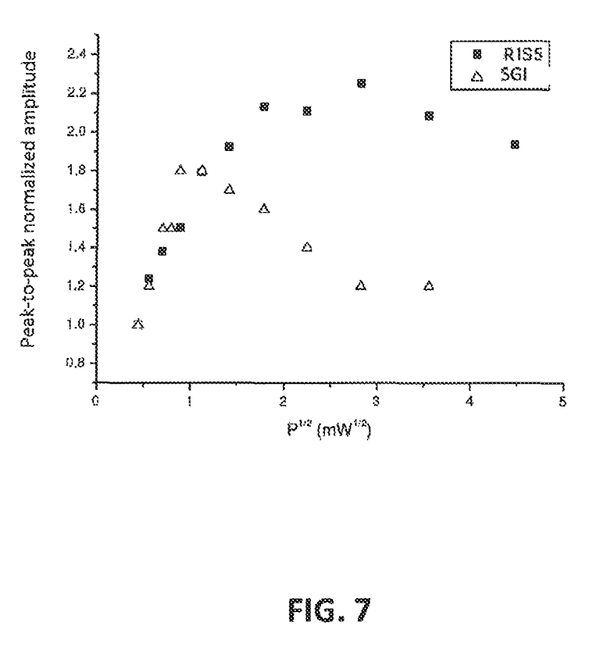
FIG. 7 illustrates the time-dependent change in the intensity of the RIS5 and SGI signals as a function of the micro-wave power to which they were subject.

3. The use of the differentiated behavior of the intensity of the intrinsic signal or of melanin and RIS5 with respect to the micro-wave power used for the EPR spectroscopy measurement like for dental enamel according to the method described in the article "Selective saturation method for EPR dosimetry with tooth enamel", E. A. Ignatiev, A. A. Romanyukha, A. A. Koshta, A. Wieser, Appl. Radiat. Isot., 47, 333-337 (1996). As visible in FIG. 7, the intensity of the intrinsic signal SGI increases with the micro-wave power until it attains a saturation point and then decreases (the figure illustrates the peak-to-peak normalized amplitudes of the RIS5 signal and of the SGI intrinsic signal versus the square root of the micro-wave power, the measurement being carried out in an X-band at room temperature with a high sensitivity resonant cavity). The saturation point of RIS5 is attained for higher values of the micro-wave power. By conducting measurements of a sample at two different micro-wave powers (low power, for example comprised between 0 and 20 mW, preferably between 0 and 10 mW and high power, for example comprised between 10 and 200 mW), it is possible to generate a system of equations with two unknowns, the solving of which allows determination of the respective amplitudes of the intrinsic signal and of the RIS5.

In the case of irradiation of only a portion of the body, the local dose may be greater than the dose received by the whole of the body by several orders of magnitude. The method of the invention is therefore particularly advantageous since it allows easy and specific determination of the dose received by the irradiated tissues. It is therefore possible for one skilled in the art to determine the risks of developing skin lesions in irradiated persons and this, even before they appear. The earlier the diagnostic, and the higher are the odds of a favorable outcome.

According to another aspect, the invention therefore deals with a process for determining risks of developing skin lesions in a subject having received external irradiation, said process including steps consisting of:

a) measuring the received dose according to the method of the invention, and b) determining depending on the dose of step a) the probability of occurrence of external lesions.

One skilled in the art considering the medical literature will be able to relate the received dose to a risk of developing skin lesions. For example, it is usually considered that an absorbed dose comprised between 3 and 10 Gy leads to erythemas, a dose greater than 3 Gy to hair loss, a dose comprised between 8 and 12 Gy to dry radioepidermitis, a dose comprised between 12 and 20 Gy to exudative radioepidermitis, a dose comprised between 20 and 25 Gy to ulceration and a dose greater than 25 Gy to necrosis of the irradiated tissues.

One skilled in the art may thus define the best therapeutic strategy to be provided depending on the nature of the dose.

The object of the invention in another aspect is therefore a method for determining the therapy to be provided to a subject having received external irradiation, said method comprising steps:

a) for determining the risks of developing skin lesions in said subject, and b) for selecting a therapy considering the risks determined in step a).

One skilled in the art may for example decide to practice medical excision of the irradiated tissues, by identifying the latter by means of the method of the invention. Alternatively, he/she may practice a cell therapy of autologous mesenchymatous stem cells. The latter should lead to the replacement of the cells killed by the irradiation with cells obtained by differentiation from said stem cells. One skilled in the art may finally decide to combine both therapies, i.e. excision and cell therapy.

The present invention further has the advantage of allowing identification in a potentially exposed population, the subjects which are more particularly in need of care. Indeed, the method of the invention also allows determination of doses of the order of one Gy. Consequently, it may advantageously be used for identifying the irradiated persons requiring immediate care or a particular follow up among said exposed population.

In this case, it may be particularly useful for one skilled in the art to refer to a dose/entire body threshold in order to determine whether a subject requires urgent care. For example, it is known that in the case of an irradiation on the entire body, the average lethal dose is 5 Gy for humans. For increasing doses, greater than 1-2 Gy, the acute irradiation syndrome is mainly expressed for the strongest doses successively by an alteration of the blood composition, a gastro-intestinal disorder and neurological disorders. Below 1 Gy, demonstrations of toxicity are more seldom but it is possible to observe a temporary lowering of the red corpuscles, of fertility and of immunity. In this respect, one skilled in the art may in particular consult the recommendations of the European project Multibiodose (www.multibiodose.eu).

Preferentially, this dose is greater than or equal to 0.5 Gy; more preferentially this dose is greater than or equal to 1 Gy; still more preferentially this dose is 2 Gy.

In order to identify the subjects requiring treatment in a potentially exposed population, it is particularly advantageous to use pre-established calibration curves for estimating the received doses. Within this scope, the measurement methods may be applied in vivo or on samples taken (ex vivo). Although this is not the only source of biological tissue sample comprising keratin which may be used in this application, nails have several advantages:

- sampling is easily carried out and in a non-invasive way;
- the analysis of samples from different portions of the body gives the possibility of determining the heterogeneity level of the dose distribution or of the irradiation configuration;
- the sensitivity of the technique is compatible with the dose levels to be measured for segregation; and
- regardless of the technique contemplated for analyzing the tissues, it is possible to conduct a large number of measurements (much greater than in conventional techniques like cytogenetics), at least of the order of a few hundred over a week as recommended by the European project Multibiodose (www.multibiodose.eu).

The invention claimed is:

1. A method (200) for determining a dose received by a sample of biological tissues comprising keratin, in particular tissues of the nail, hair or skin-cornea type, the method comprising:
    a) applying a measurement of radio-induced signal, followed by irradiation of the sample, in a repeated way until an intensity reference level of the signal is attained, the sample being prepared after each of said irradiations by hydration of the sample for a period of more than 5 minutes and controlled dehydration of the sample,
    b) determining an absolute value of received dose (230) by at least one reference sample, corresponding to the intensity reference level of the signal, and
    c) determining the dose level initially received (240) by the first sample as being the subtraction, from the value of the dose received by the reference sample, of the total dose added to the initial dose of the first sample during the application of step a).

2. The method for determining a dose according to claim 1, wherein the intensity reference level of the signal is a saturation level of the intensity of the signal with the received dose or annihilation level of the signal.

3. The method for determining a dose according to claim 1, further comprising a preliminary step comprising:
    applying a measurement of radio-induced signal on the sample for which the intention is to determine the dose received for obtaining a first signal intensity,
    irradiation of the sample at a dose of less than 5 Gy, preferably less than 1 Gy,
    applying a second measurement on the sample in order to obtain a second signal intensity, and
    comparison of the intensities of both intensities for inferring therefrom an estimation of initial dose level received by the sample relatively to a dose level corresponding to a saturation level of the signal intensity.

4. The method for determining a dose according to claim 1, wherein the technique for measuring the radio-induced signal intensity applied is EPR spectroscopy or measurement by luminescence.

5. The method for determining a dose according to claim 1, wherein the step b) of determining a dose value received by a reference sample corresponding to the reference level of signal intensity is applied from a curve relating absolute values of doses received by the reference sample with signal intensity levels, said curve being produced:
    by averaging curves generated from measurements on biological tissues from a plurality of individuals,
    from measurements conducted on non-irradiated biological tissues from the same individual as the first sample, or
    from measurements conducted on irradiated biological tissues from the same individual as the first sample, said measurements being applied by measuring thermoluminescence after step a), and the first sample having been heated between step a) and said measurements for suppressing the initial radio-induced signal.

6. The method for determining a dose according to claim 5, wherein each curve is generated by one of the following processes:
    cutting out a reference sample into a plurality of fragments and applying, on the fragments, irradiations at distinct and determined doses, and measuring a radio-induced signal intensity in the sample for each dose,
    applying successive irradiations of the reference sample at known doses, each irradiation being followed by a measurement of radio-induced signal intensity, or
    applying successive irradiations at distinct and determined doses, each irradiation being followed by a measurement of radio-induced signal intensity by measuring thermoluminescence, and then by heating of the sample for suppressing the radio-induced signal.

7. A process for determining risks of developing skin lesions in a subject having received external irradiation, said process including steps consisting of:
    i. determining the received dose according to claim 1, and
    ii. determining depending on the dose of step i) the probability of occurrence of external lesions.

8. A method for determining a dose received by a sample by applying a process with dosed additions or by comparison of a radio-induced signal of the sample measured by EPR spectroscopy or by luminescence measurement with a pre-established calibration curve, characterized in that it comprises, for each radio-induced signal measurement conducted on a sample prepared by:
    hydration of the sample for a period of more than 5 minutes, and
    controlled dehydration of the sample, the determination of the contributions of the intrinsic signal (SGI) of the sample and of the signal of a radio-induced radical species (RIS5) having, during the measurement of a biological tissue sample of the nail, hair or skin-cornea type by EPR spectroscopy in continuous waves at room temperature:

a Landé factor of 2.004, during measurements in a Q-band and at room temperature, a minimum signal intensity and a maximum signal intensity, said intensities being attained for magnetic field values separated by 1.8 mT, during measurements in a X-band, a signal forming a singlet, and at a higher frequency, a signal having a Landé factor anisotropy.

9. The method for determining according to claim 8, wherein the tissue sample is a sample of nails, and the determination of the contributions of the intrinsic signal (SGI) of the sample and of the radio-induced radical species (RIS5) comprises the measurement of a radio-induced signal of the sample for a same dose received by the sample, after two distinct hydration periods, and the inference, from the measurements, of the contributions of the intrinsic signal (SGI) and of the radio-induced species signal.

10. The method for determining according to claim 8, wherein the tissue sample is a sample of nails, and the determination of the contributions of the intrinsic signal (SGI) of the sample and of the radio-induced radical species (RIS5) comprises the measurement of a radio-induced signal of the sample before and after exposure to a beam of ultrasonic waves for a determined duration, and the inference of said contributions from the measurements.

11. The method for determining according to claim 8, wherein the determination of the contributions of the intrinsic signal (SGI) of the sample and of the radio-induced radical species (RIS5) comprises the measurement of a radio-induced signal of the sample after exposure to micro-waves at a first power, and exposure to micro-waves at a second power, greater than the first, and the inference of said contributions from the measurements.

* * * * *